(12) United States Patent
Ward

(10) Patent No.: US 10,856,588 B2
(45) Date of Patent: *Dec. 8, 2020

(54) SENSING GARMENTS

(71) Applicant: Purdue Research Foundation, West Lafayette, IN (US)

(72) Inventor: Eric Ward, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/288,993

(22) Filed: Feb. 28, 2019

(65) Prior Publication Data

US 2019/0191786 A1  Jun. 27, 2019

Related U.S. Application Data

(63) Continuation of application No. 15/950,448, filed on Apr. 11, 2018, now Pat. No. 10,251,429, which is a continuation of application No. 14/782,871, filed as application No. PCT/US2014/033435 on Apr. 9, 2014, now Pat. No. 9,968,141.

(60) Provisional application No. 61/810,496, filed on Apr. 10, 2013.

(51) Int. Cl.
| | |
|---|---|
| *G01N 1/22* | (2006.01) |
| *A41D 1/00* | (2018.01) |
| *A41D 13/00* | (2006.01) |
| *A61B 5/00* | (2006.01) |
| *A41D 1/04* | (2006.01) |
| *A41D 27/20* | (2006.01) |
| *A61B 5/097* | (2006.01) |
| *A61B 5/11* | (2006.01) |
| *G01N 33/00* | (2006.01) |

(52) U.S. Cl.
CPC .............. *A41D 1/002* (2013.01); *A41D 1/04* (2013.01); *A41D 13/0012* (2013.01); *A41D 27/201* (2013.01); *A41D 27/205* (2013.01); *A61B 5/6805* (2013.01); *G01N 1/2273* (2013.01); *A61B 5/097* (2013.01); *A61B 5/1113* (2013.01); *A61B 2560/0242* (2013.01); *G01N 33/0057* (2013.01); *G01N 2001/2276* (2013.01)

(58) Field of Classification Search
CPC .............. A61B 5/6805; G01N 1/2273; G01N 2001/2276; A41D 1/002; A41D 27/205; A41D 13/1281; A41D 1/005; A41D 13/0012; A41D 1/04; A41D 3/00
See application file for complete search history.

(56) References Cited

U.S. PATENT DOCUMENTS

| | | | | |
|---|---|---|---|---|
| 2,156,504 A | * | 5/1939 | Liss ...................... | A41D 13/12 2/312 |
| 2,426,726 A | * | 9/1947 | Combs .................. | A41D 7/003 441/102 |
| 4,187,859 A | | 2/1980 | Allen et al. | |

(Continued)

OTHER PUBLICATIONS

International Search Report and Written Opinion dated Aug. 27, 2014, for International Patent Application No. PCT/US2014/033435, filed Apr. 9, 2014 (14 pages).

*Primary Examiner* — Tajash D Patel
(74) *Attorney, Agent, or Firm* — Brown Rudnick LLP; Adam M. Schoen

(57) ABSTRACT

The invention generally relates to sensing garments.

9 Claims, 17 Drawing Sheets

(56) References Cited

U.S. PATENT DOCUMENTS

| | | | | |
|---|---|---|---|---|
| 4,504,267 A * | 3/1985 | Parmelee | ............... | A61M 5/148 604/134 |
| 4,539,700 A * | 9/1985 | Sato | ....................... | H04R 5/023 224/230 |
| 4,589,134 A * | 5/1986 | Waldron | ................... | H04R 5/02 381/301 |
| 4,666,432 A * | 5/1987 | McNeish | ............... | A61M 25/02 128/DIG. 26 |
| 5,484,366 A | 1/1996 | Wilkinson | | |
| 5,617,582 A | 4/1997 | Burwell | | |
| 5,722,573 A * | 3/1998 | Carnel | ....................... | A45F 3/16 224/148.2 |
| 5,810,699 A | 9/1998 | Nadeau | | |
| 6,097,822 A * | 8/2000 | Min | ....................... | H04R 5/023 2/102 |
| 6,286,146 B1 | 9/2001 | Rocker | | |
| 6,314,580 B1 | 11/2001 | Greenberg et al. | | |
| 6,826,782 B2 | 12/2004 | Jordan | | |
| 7,364,491 B2 * | 4/2008 | Updyke | ............... | A41C 3/0035 2/247 |
| 7,490,361 B1 | 2/2009 | Floyd | | |
| 8,262,545 B1 | 9/2012 | Beber et al. | | |
| 8,607,366 B2 * | 12/2013 | Austin | ............... | A41D 13/1236 2/300 |
| 8,818,478 B2 * | 8/2014 | Scheffler | ............ | A41D 13/1281 600/388 |
| 9,968,141 B2 | 5/2018 | Ward | | |
| 10,251,429 B2 | 4/2019 | Ward | | |
| 2005/0096199 A1 | 5/2005 | Egbert et al. | | |
| 2005/0177056 A1 | 8/2005 | Giron et al. | | |
| 2006/0117453 A1 | 6/2006 | Hood | | |
| 2006/0276717 A1 | 12/2006 | Mossanen-Shams | | |
| 2007/0073131 A1 | 3/2007 | Ryu et al. | | |
| 2011/0043755 A1 | 2/2011 | Gibson-Horn et al. | | |
| 2013/0000021 A1 | 1/2013 | Dolcetti | | |
| 2016/0015104 A1 | 1/2016 | Edwards et al. | | |
| 2018/0021605 A1 | 1/2018 | Bartkoski | | |

* cited by examiner

SENSING GARMENTS

RELATED APPLICATION

The present application is a continuation of U.S. nonprovisional patent application Ser. No. 15/950,448, filed Apr. 11, 2018, which is a continuation of U.S. nonprovisional patent application Ser. No. 14/782,871, filed Oct. 7, 2015, which is a 35 U.S.C. § 371 national phase application of PCT/US14/33435, filed Apr. 9, 2014, which claims the benefit of and priority to U.S. provisional patent application Ser. No. 61/810,496, filed Apr. 10, 2013, the content of each of which is incorporated by reference herein in its entirety.

FIELD OF THE INVENTION

The invention generally relates to sensing garments.

BACKGROUND

Industrial hygiene monitoring also known as exposure monitoring is a process of evaluating and documenting employee potential exposures to biological, chemical and/or physical hazards. Monitoring can be qualitative or quantitative. Qualitative assessments involve observing the operation and the employee and noting the potential hazards. Based on those assessments, determinations are made if further evaluation is necessary. Quantitative assessments involve a sensing device that samples the worker's environment. Collected data is sent for laboratory analysis to determine if the average airborne concentration of a particular chemical agent or noise level poses a potential hazard. During that process, an employee wears the sampling equipment so their exposure during their normal work-shift can be determined.

There are numerous problems associated with wearing of the sampling equipment. For example, attaching a piece of equipment to an article of clothing can result in the equipment tugging on the article of clothing during the worker's day. Additionally, attachments to the equipment including wires, hoses, etc., can snag on various items resulting in the equipment becoming tangled, damaged, or separated from the article of clothing. Those problems result in workers not wanting to wear the sampling equipment, and many workers remove the sampling equipment at some point during their workday. Removal of the equipment leads to skewed results and requires re-sampling, costing a company time and money.

Another problem with simply clipping the sampling equipment to the clothing of the worker is that sampling equipment may shift during the workday. Because environmental conditions are not homogeneous at a work site (e.g., conditions around a worker's feet or waist are different than conditions around a worker's personal breathing zone (the approximate 9 inch circumference around a worker's head)), shifting of the sampling equipment causes the equipment to register different results based on the location from which the device samples the environment. Obtaining results from outside a worker's personalized breathing zone also skews results and also requires re-sampling.

SUMMARY

The invention provides a wearable garment that is configured to integrate a sensing device into the garment. The garment is configured to counter-balance weight of a sample device, thereby evenly distributing weight about the garment. It may also be configured to releasably hold a sensing device, to retain components of the sensing device to the garment, and to position a distal end of the sampling device within a personal breathing zone of a wearer. In this manner, the invention provides a garment that seamlessly integrates the sensing device into the garment, is ergonomically balanced, and ensures that samples are consistently measured in the personal breathing zone of individuals.

In certain aspects, the invention provides an article of clothing that includes a wearable garment. The garment includes at least one portion that is configured to receive and releasably retain at least one sensing device. The garment also includes one or more weights coupled to the garment, in which the article of clothing is configured such that the weights counter-balance the sensing device. In this manner, the weight of the garment is evenly distributed about the garment so that it wears like any other article of clothing. Accordingly, a worker does not have a sensation of tugging or pulling for the sensing device as the worker carries on during the workday.

The article of clothing is configured to releasably retain a sensing device. In that manner, the article of clothing acts as platform in which different sensors can be freely and easily interchanged into and out of the article. Accordingly, individuals can use any specific sensors and couple them into and remove them from the article. Any releasable retaining mechanism can be used with the invention. For example, pockets, hooks, clips, Velcro, etc. In certain embodiments, the article of clothing is configured with a pocket, that may optionally have a flap that is configured to releasably hold the sensing device. The retaining feature may be positioned anywhere on the article of clothing. The weights may be releasable coupled to the garment by any means known in the art, for example by clips, hooks, Velcro, or adhesives. In certain embodiments, the weights are integrated between inner and outer layers of the garment. The position of the weights is determined by the position of the retaining feature. For example, if the retaining feature is positioned on a back of the garment, the weights will be positioned on a front and optionally sides of the article of clothing. In alternative embodiments, if the retaining feature is positioned on a front of the garment, the weights will be positioned on a back and optionally sides of the article of clothing.

In other aspects, the invention provides an article of clothing that includes a wearable garment and at least one sensing device. Typically, the sensing device includes a body coupled to a conduit, and the garment is configured to releasably hold the body of the sensing device, to retain the conduit to the garment, and to position a distal end of the conduit within a personal breathing zone of a wearer. In this manner, garments of the invention hold the sensing device snug to the article of clothing and prevent components of the sensing device from becoming tangled, damaged, or separated from the article of clothing. Additionally, garments of the invention ensure that samples are consistently measured in a standardized position within the personal breathing zone of individuals in the sample population wearing the garment.

Any retaining mechanism known in the art may be used to retain the conduit to the garment and to position a distal end of the conduit within a personal breathing zone of a wearer. In certain embodiments, the garment includes an open channel between inner and outer layers of the garment, and the conduit passes through the channel from the portion that hold the body of the sensing device to a distal opening of the channel at a top portion of the garment such that a distal end of the conduit is within the personal breathing zone of the wearer. In other embodiments, the article of clothing includes a plurality of tabs attached to an outer layer of the garment, and the conduit passes through the tabs from the portion that holds the body of the sensing device such that a distal end of the conduit is within the personal breathing zone of the wearer. The conduit will depend on the type of sensing device employed. Exemplary conduits include a tube or an electrical wire. For example, if the sensing device is a sampling pump that holds a collection media, the conduit is a hollow tube that couples to the pump. If the sensing device is a noise dosimeter, then the conduit is a wire that couples to a microphone at a distal end of the device.

The garments of the invention may be any article of clothing, such as vests, jackets, pants, shorts, short-sleeve shirts, long-sleeve shirts, sweaters, sweat shirts, wind breakers etc. In certain embodiments, the article is a vest. The sensing device may be any device that interacts with the environment. Example devices include a sampling pump, a noise dosimeter, a radiation sensor, a chemical sensor (including filter cassettes, charcoal tubes, and devices which only allow particles of a certain size to be collected), a biological agent sensor (including filter cassettes, charcoal tubes, and devices which only allow particles of a certain size to be collected), and/or a video camera. Articles of clothing of the invention may include additional features, such as reflective material, lights (such as strobe lights), and other safety features.

In other embodiments, the invention provides an article of clothing that includes a wearable garment and at least one sensing device integrated into the garment. There are one or more weights coupled to the garment and the article of clothing is configured such that the weights counter-balance the sensing device.

In still other embodiments, a multi-sensing article of clothing is provided. In such embodiments, the article of clothing is configured to integrate a plurality of sensing devices. Multi-sensing articles generally include a wearable garment including a plurality of portions that are each configured to receive and releasably retain at least one sensing device. In such embodiments, weights are not required, although can optionally be used, for counter-balancing. Rather, the plurality of portions are arranged about the garment such that the sensing devices counter-balance each other. Optionally, and not required, weights can also be coupled to the garment to help with counter-balancing.

In other embodiments, the invention provides a wearable garment, and a plurality of sensing devices integrated into the garment, in which the plurality of sensing devices are integrated about the garment such that the sensing-devices counter-balance each other. Optionally, and not required, weights can also be coupled to the garment to help with counter-balancing.

Any of the embodiments and aspects of the invention described herein can be combined with each other. For example, in a particular embodiment, a single wearable garment includes a plurality of portion, each configured to releasably retain a sensing device or the garment integrates a plurality of sensing devices, or a combination thereof such that some sensing devices are integrated into the garment and some are coupled to garment via the releasable retaining portions. The garment is configured such that the load of the garment is equally distributed about a user by having the sensing devices distributed about the garment so that they counter-balance each other, optionally with the help of weights or only with weights. The garment is configured to retain components of the sensing device to the garment, and to position a distal end of the sampling device within a personal breathing zone of a wearer. In this same embodiment, the garment may be flame retardant, may be configured as a "break-away" garment as explained below, may include a camera, and may also include a positioning sensor, such as an radio frequency identification (RFID) tag.

DETAILED DESCRIPTION

The invention generally relates to sensing garments. In certain aspects, the invention provides an article of clothing that includes a wearable garment. The garment includes at least one portion that is configured to receive and releasably retain at least one sensing device. The garment also includes one or more weights coupled to the garment, in which the article of clothing is configured such that the weights counter-balance the sensing device. In other embodiments, weights do not have to be used (although can be used); rather, the garment is configured with a plurality of portions, each of which is configured to releasably retain a plurality of sensing devices. In such embodiments, the plurality of portions are arranged about the garment such that the sensing devices counter-balance each other. In other aspects, the invention provides an article of clothing that includes a wearable garment and at least one sensing device. Typically, the sensing device includes a body coupled to a conduit, and the garment is configured to releasably hold the body of the sensing device, to retain the conduit to the garment, and to position a distal end of the conduit at selected location on the garment. One selected location may be within a personal breathing zone of a wearer, on the back of a wearer, on the side of a wearer, or on the front of a wearer. In other aspects, the sensing device(s) are integrated (e.g., permanently integrated) into the garment. In such embodiments, the devices are arranged in the garment to counter-balance each other, optionally with the help of weights. As mentioned above, any of the embodiments and aspects of the invention described herein can be combined with each other. Additionally, while only exemplified with a single or six sensing devices, articles of the invention can be equipped with any number of sensing devices.

The garments of the invention may be any article of clothing, such as vests, jackets, pants, shorts, short-sleeve shirts, long-sleeve shirts, sweaters, sweat shirts, wind breakers etc. In certain embodiments, the article is a vest. The sensing device may be any device that interacts with the environment. Example devices include a sampling pump, a noise dosimeter, a radiation sensor, a chemical sensor, a biological agent sensor, physiological health sensors, and/or a video camera. Articles of clothing of the invention may include additional features, such as reflective material, lights (such as strobe lights), and other safety features.

Figure 1:
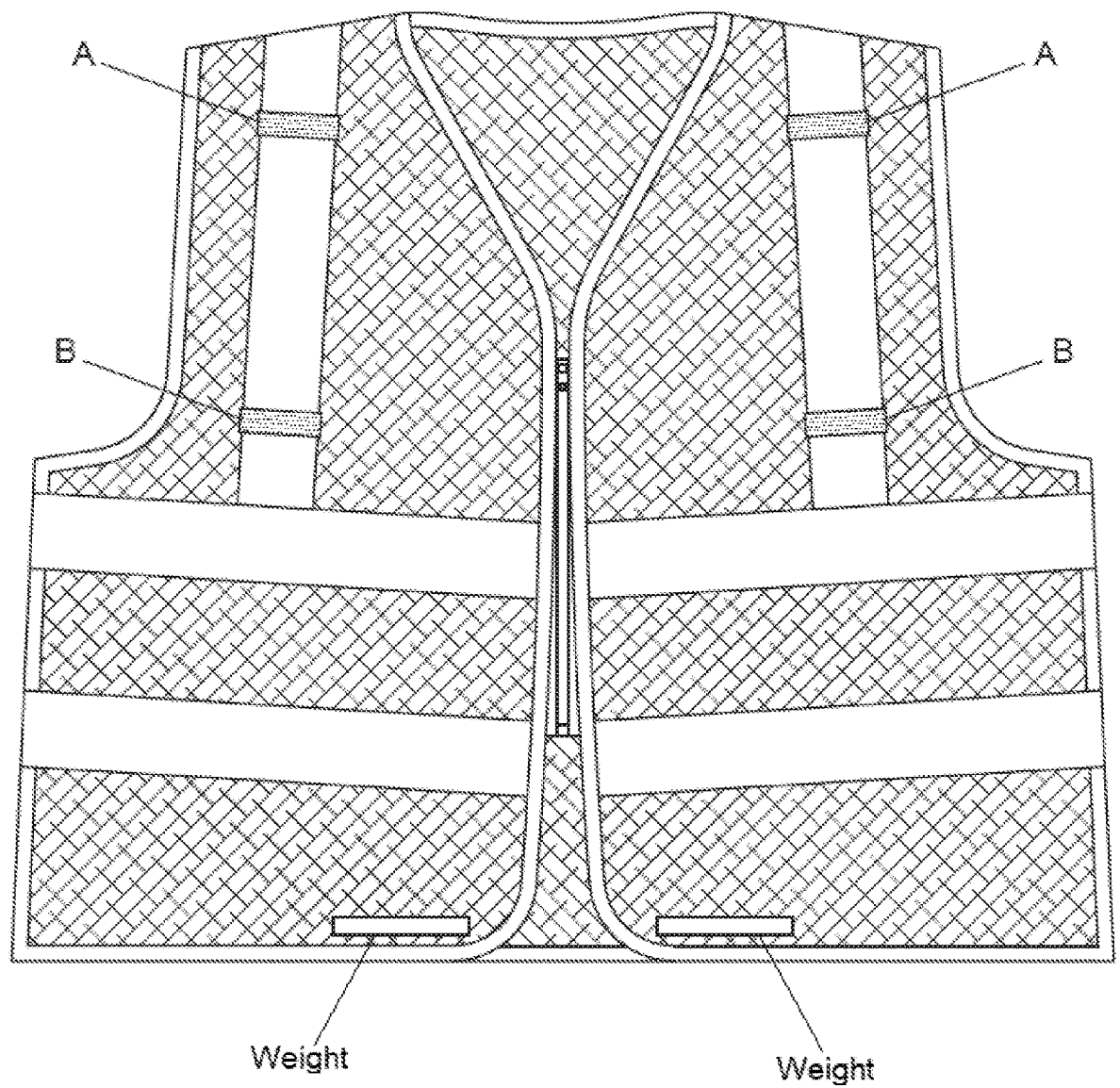
FIG. 1 depicts a front view of an embodiments of articles of clothing of the invention.
Figure 4:
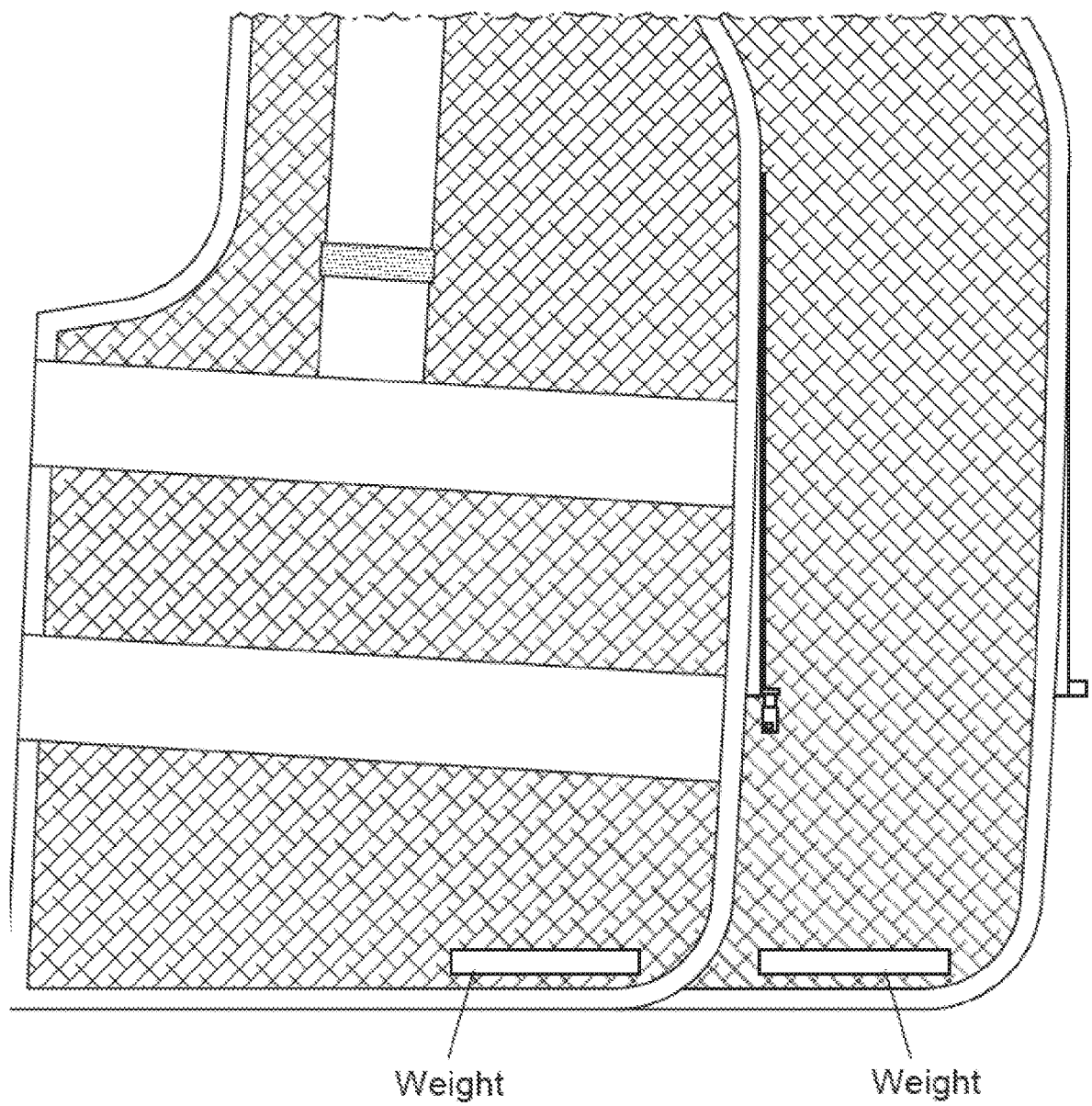
FIG. 4 depicts an embodiments showing weights integrated between inner and outer layers of an article of clothing of the invention.

FIG. 1 shows an exemplary embodiment of an article of clothing of the invention. In this embodiment, the article of clothing is shown as a vest and the vest includes reflective material. The reflective material is optional, and the vest is only an exemplary article of clothing. The vest shown in FIG. 1 is ergonomically balanced on the user by counter weights on a bottom front portion of the vest, as is disclosed in FIG. 4. In this embodiment, the vest includes straps that are capable of holding a conduit of the sensing device (e.g., tubing and/or wiring) against the vest and out of the way of the user. On of skill in the art, will understand that straps are not a required component of this embodiment, and that the use of straps for retaining the conduit of the sensing device is only exemplary. Any retaining mechanism known in the art may be used to retain the conduit to the garment and to position a distal end of the conduit at a selected location on the wearer, for example within a personal breathing zone of a wearer. For example, in another embodiment, the vest includes integrated airtight channels and/or cables that are configured to provide a plug-in capability between the equipment that can be attached and an attachment unit, e.g., a sensor, an input/output (I/O) device, etc.

The vest, which can range in size from child extra small to adult male four extra-large, includes a portion that is configured to receive and releasably retain at least one sensing device. Any retaining mechanism can be used with the invention. For example, pockets, hooks, clips, Velcro, etc. In the exemplary embodiment shown in FIG. 1, the portion is a padded, closeable pocket with a volume of 1 cubic inch to 1 cubic foot and straps 1 to 6 inches long and 0.01-6 inches wide. In this exemplary embodiment, the pocket is shown on the back middle of the vest. Other placements, such as either side or the front may be used. Additionally, the retaining feature may be placed higher or lower on the vest.

Figure 2:
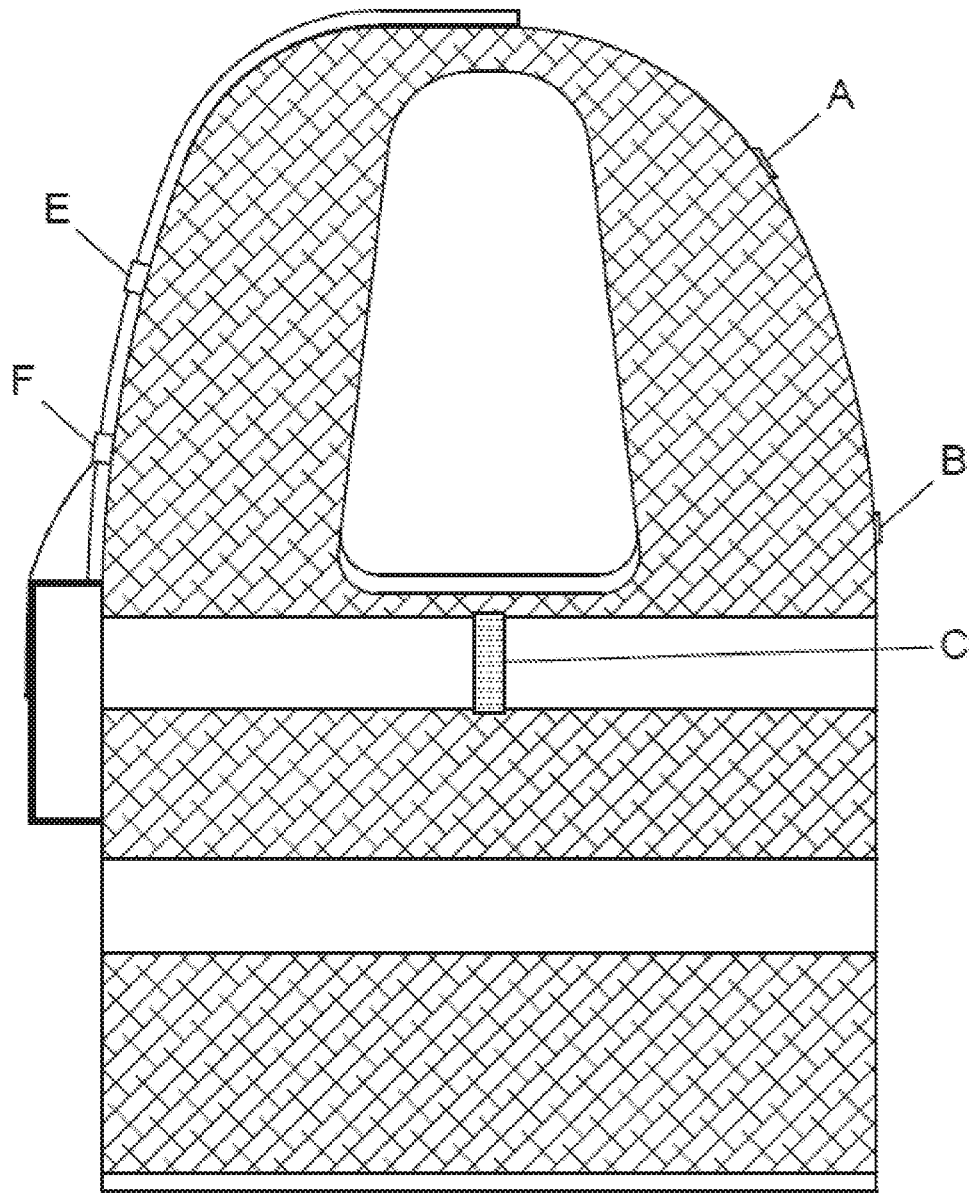
FIG. 2 depicts a side view of the article shown in FIG. 1.
Figure 3:
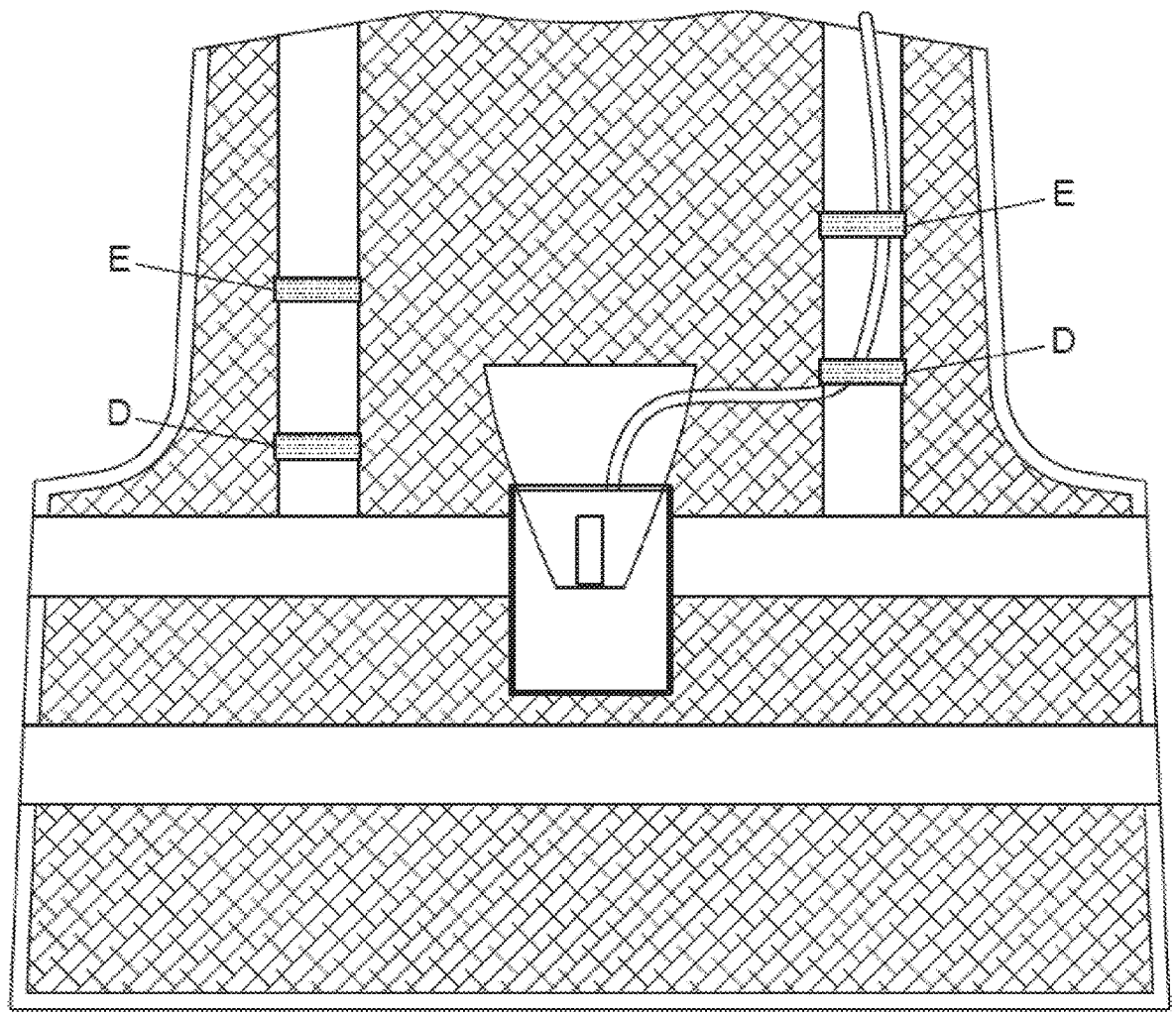
FIG. 3 depicts a back view of the article shown in FIG. 1.

In the exemplary embodiment shown in FIG. 1, the placement of the straps A is arranged near the center of the upper shoulder area of the front of the vest. The placement of straps B (see FIG. 1) is provided on the front side of the vest, above the bottom of the arm hole and below straps A. The placement of straps C (see FIG. 2) is provided under the arm hole of the vest on the side portion of the vest. The placement of straps D (see FIG. 3) is provided above the pocket near the arm hole below straps E. The placement of straps E (see FIG. 3) is provided on the back portion of the vest below the shoulders and above straps D. Such a configuration is only exemplary, and other placements of the straps may be used with articles of the invention.

In the exemplary embodiment show in FIG. 1, the vest includes weights. The weights may be releasably coupled to the garment by any means known in the art, for example by clips, pockets, hooks, Velcro, or adhesives. In certain embodiments, the weights are integrated between inner and outer layers of the garment. The position of the weights is determined by the position of the retaining feature. For example, if the retaining feature is positioned on a back of the garment, the weights will be positioned on a front and optionally sides of the article of clothing. In alternative embodiments, if the retaining feature is positioned on a front of the garment, the weights will be positioned on a back and optionally sides of the article of clothing. The value for each weight will depend on the number of weights used and the weight of the sensing device. In the embodiment shown in FIG. 1, the vest includes a pair of weights that range from 0.01 to 5 pounds each and that can be placed on the front bottom portion of the vest. In this manner, articles of clothing of the invention advantageously provide ergonomic weight distribution. Since an individual wearing the vest is more likely to keep the vest on due to its ergonomic nature, environmental sampling, such as sampling of air, becomes more representative of the person's environment, e.g., air intake.

The vest shown above in FIGS. 1-4 can be made by attaching ten 2" straps (A-E), padded closeable pocket with an approximate volume of 30 cubic inches, and two 0.01 to 2 lb weights to a class 2 safety vest. The following includes steps according to one embodiment for assembly and making of the vest. First attach the pocket in the center of the back of the vest, so that the bottom of the pocket is between 7-8 inches from the bottom of the vest. Next, attach straps D 3-4 inches above and to the right and left of the top of the pocket. Next, attach straps E approximately 5-7 inches above straps D. Next attach straps C so that they are 1-3 inches below the center of the arm holes. Next attach straps A, so that they are in the center of the shoulder area 1-3 inches below the top front portion of the vest. Next, attach straps B 8-10 inches below straps A. Lastly; attach the weights on the front inside bottom portion of the vest.

The vest ergonomically balances the weight of the device in the pocket by counter weights in the front of the vest, creating a comfortable experience for the wearer since the weight of the device is balanced and does not tug on the clothing of the user. The vest holds the tubing/wiring close to the vest minimizing the amount of material which hangs on the user and could potentially snag or be caught in machinery. The vest also ensures that air samples are consistently measured from a standardized position within the personal breathing zone of individuals in the sample population wearing the vest. Since, the vest eliminates inconsistency caused traditionally by an Industrial Hygienist placing the media sample from a non-standardized position in the personal breathing zone, any difference in concentrations derived from the analysis of the media cannot be attributed to the placement of the media sample resulting in more accurate assessment of the individual's exposure measurements. A standardized placement means that the vest is configured to placing the sensing device at the same location regardless of the user, whatever that location within the breathing zone may be. For example, the standardized location may be 5 inches from the nose of the user, or 3 inches from the mouth of the user, or 5 inches to either side of the head of the user. The specific location does not matter, as long as the sensing device can be positioned in the same location in relation to any user.

Figure 5:
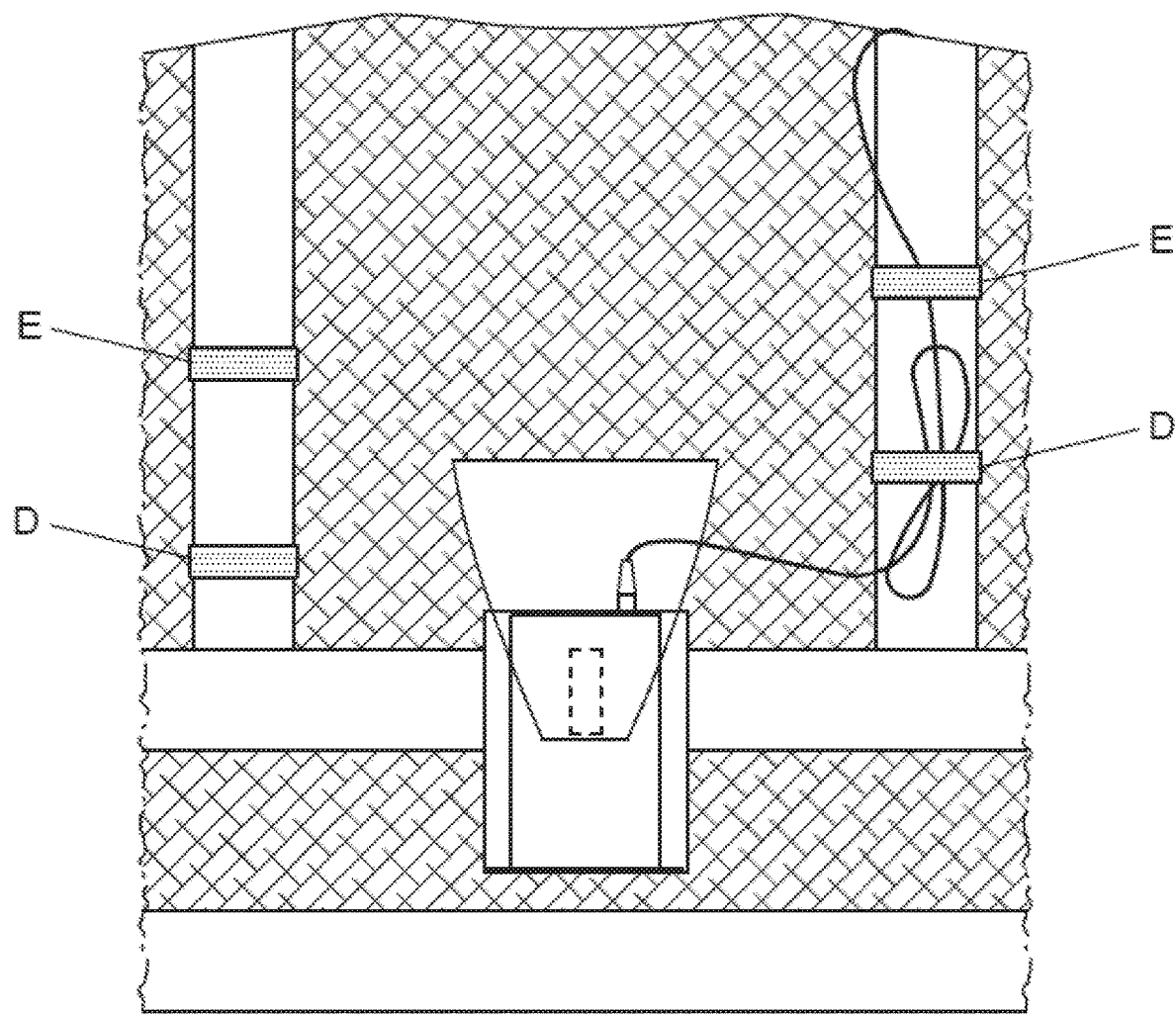
FIG. 5 depicts an embodiments showing a noise dosimeter as the sensing device. The Figure shows a body of the sensing device held in the article.
Figure 6:
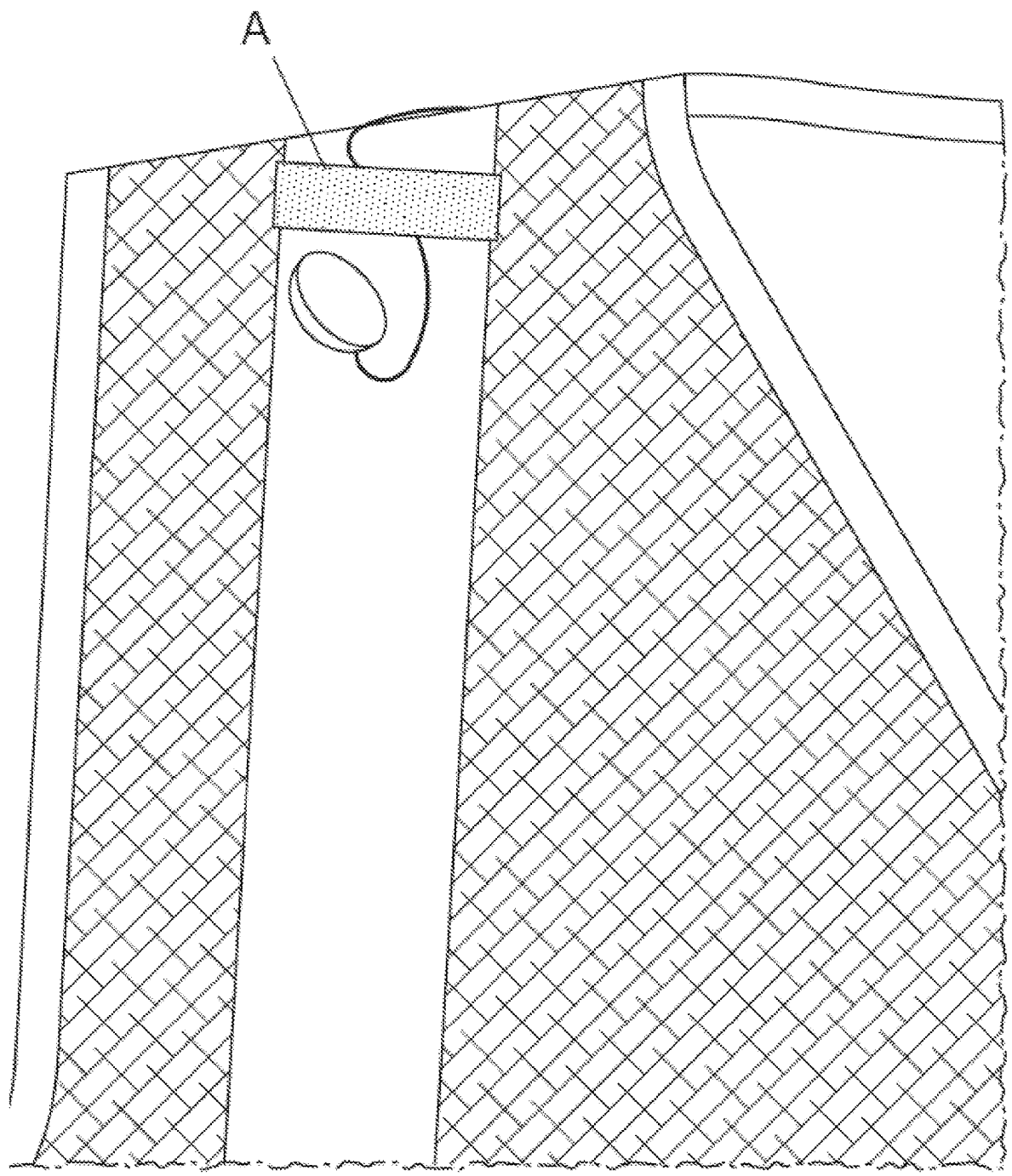
FIG. 6 depicts another view of the article shown in FIG. 5. The Figures shows a microphone of the sensing device held by the article in the personal breathing zone of a wearer.

Additional views of the vest are provided in FIGS. 5-6. Those figures show an embodiment in which the sensing device is a noise dosimeter. FIG. 5 shows the body of the device in the pocket of the vest. The wire conduit is held snug to the vest via straps E and D. Any excess wire is coupled to the vest, for example by attaching it to strap D as shown in FIG. 5. FIG. 6 shows the microphone coupled to the wire conduit and attached to the vest within the personal breathing zone of the wearer.

In other embodiments, the garment may include a plurality of portions, each configured to releasably retain a sensing device. For example, garments of the invention may include two portions, three portions, four portions, five portions, six portions, seven portions, eight portions, nine portions, ten portions, 15 portions, 20 portions, etc. FIGS. 10-21 show different views of a six pocket vest of the invention. As already mentioned, six pockets is exemplary, and not limiting, of the number of pockets that may be used in garments of the invention. Additionally, pockets are exemplified as exemplary releasable retaining portions, and other releasable retaining mechanisms as discussed above can be used with garments of the invention. Even further, the vest shown in FIGS. 10-17 is only an exemplary garment, and other garment, such as patents, coats, shirts, etc., are included as embodiments of the invention.

Figure 10:
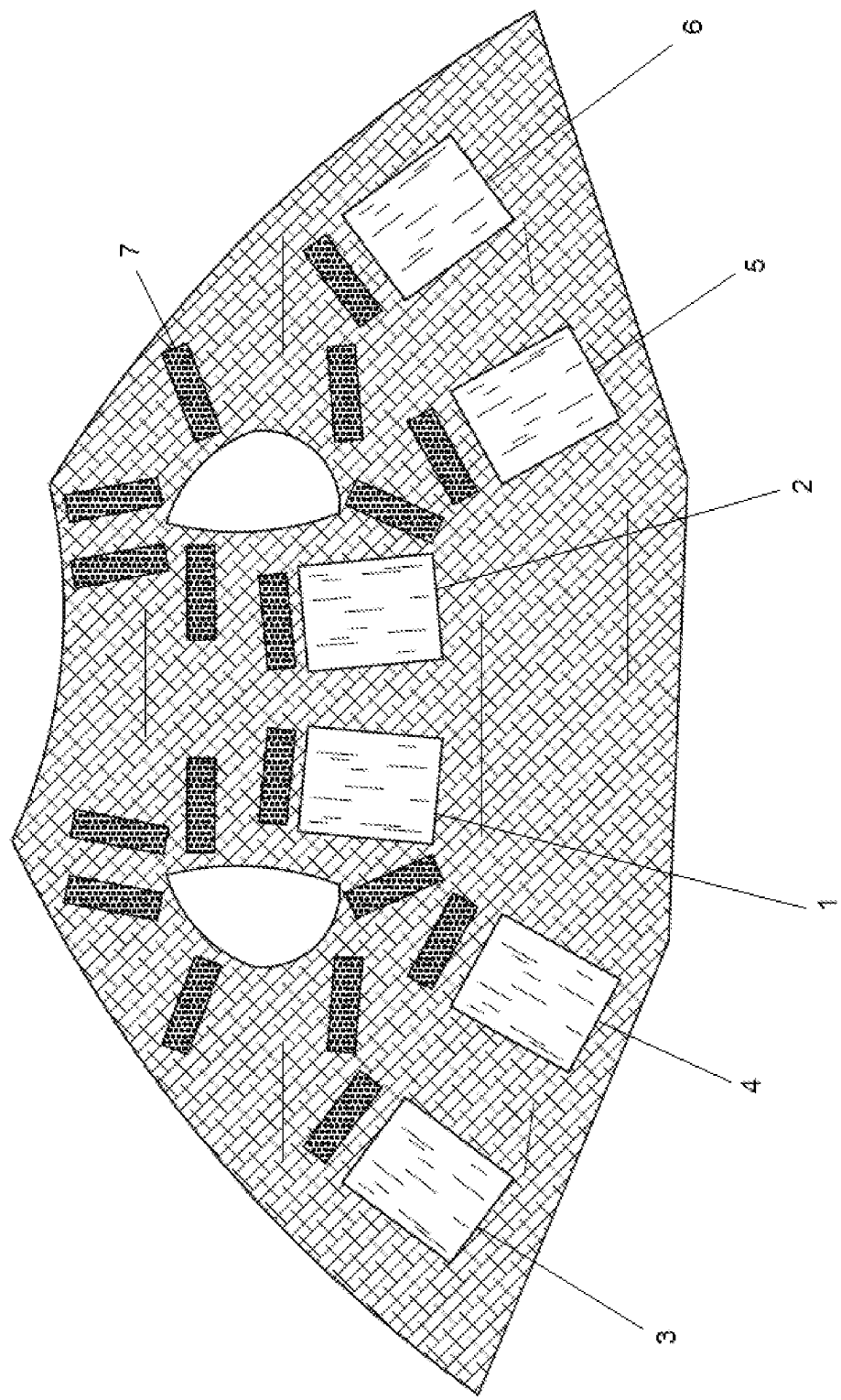
FIG. 10 depicts is a back view of an unfolded vest of another embodiment of articles of clothing of the invention. This embodiment illustrates 6 portions of the vest (pockets) arranged about the garment such that the sensing-devices, when inserted into those portions of the vest, counter-balance each other
Figure 11:
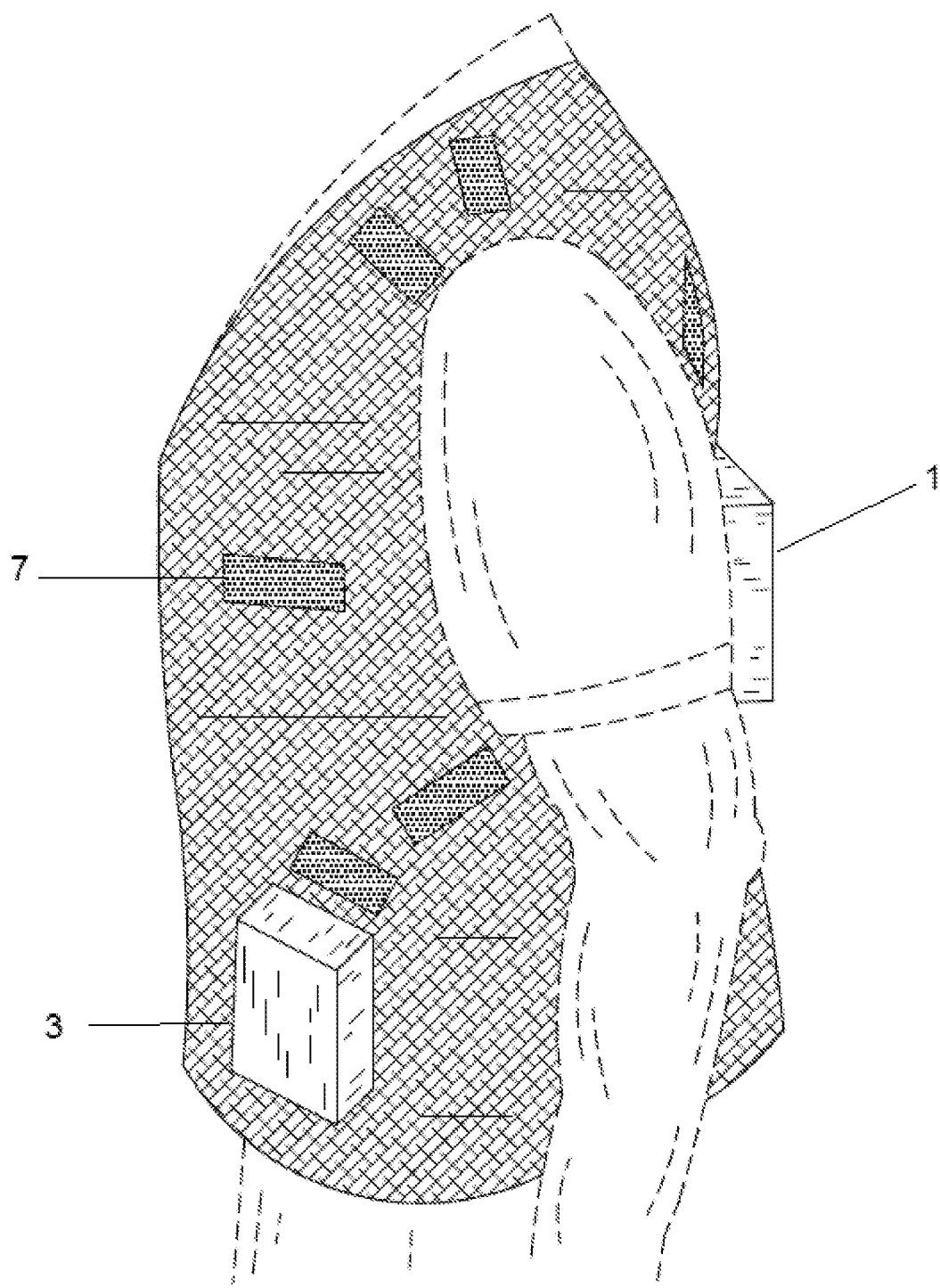
FIG. 11 depicts a left side view of the article shown in FIG. 10 being worn by a user.
Figure 12:
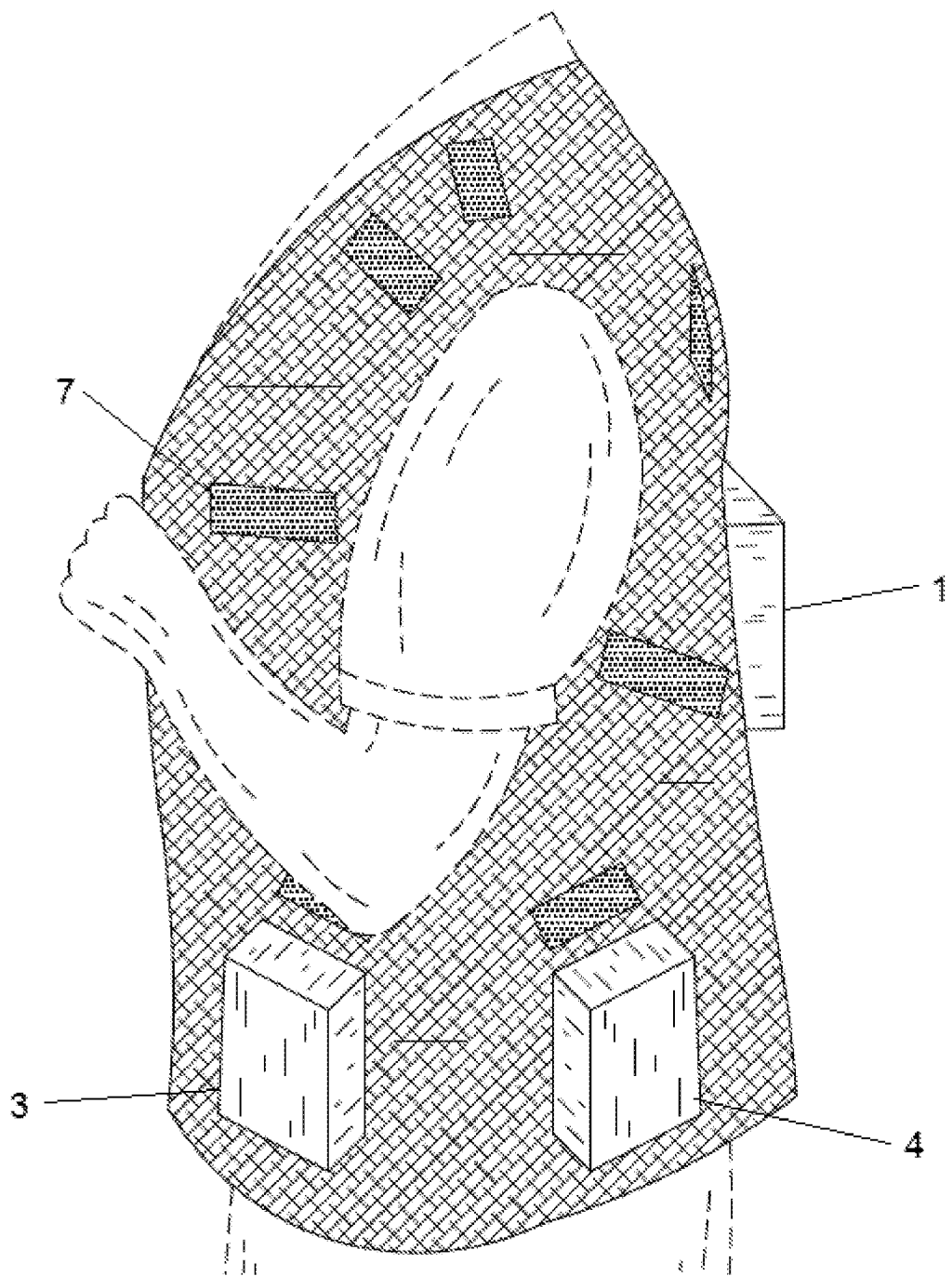
FIG. 12 depicts another left side view of the article shown in FIG. 10 being worn by a user.
Figure 13:
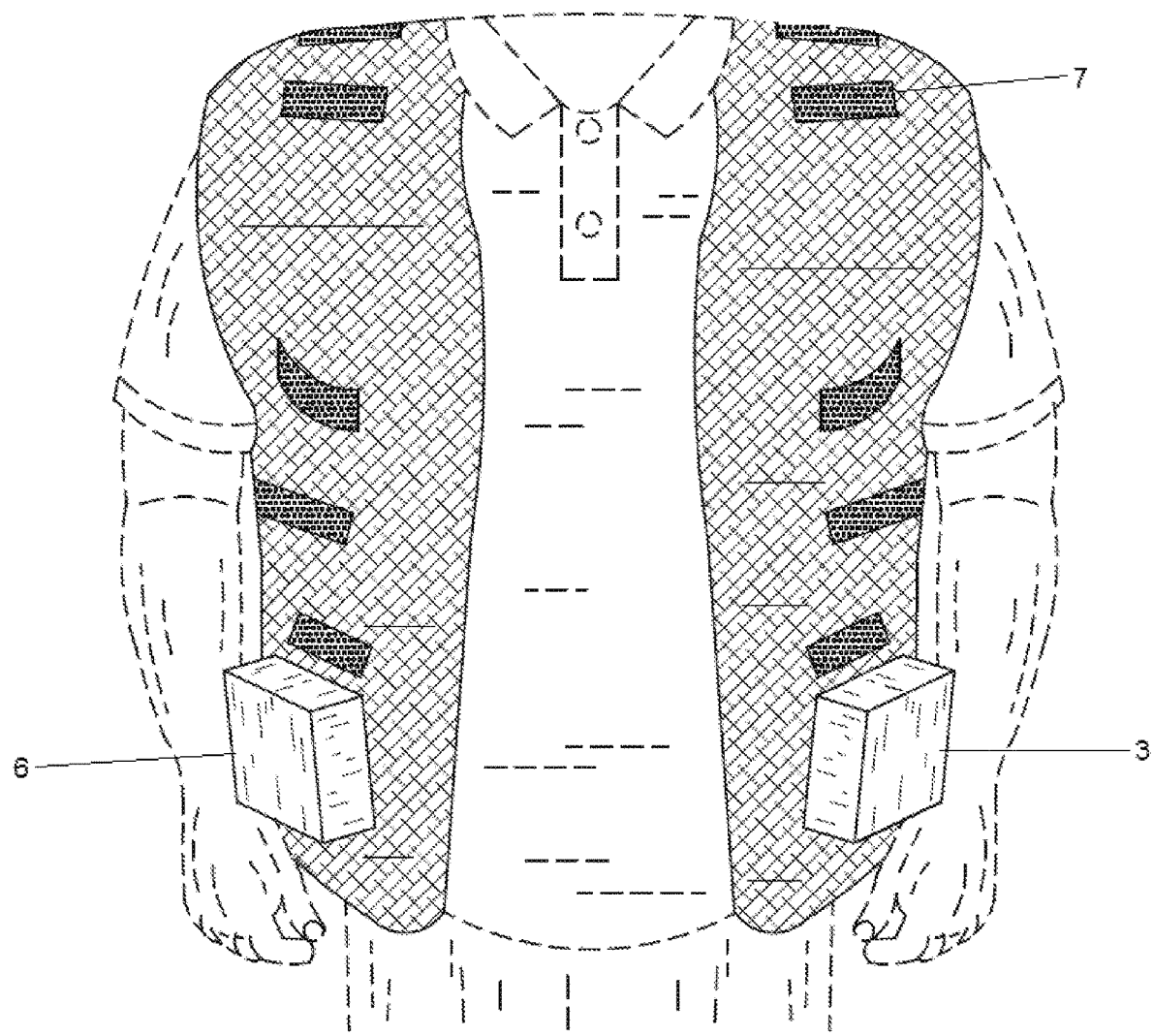
FIG. 13 depicts a front side view of the article shown in FIG. 10 being worn by a user.
Figure 14:
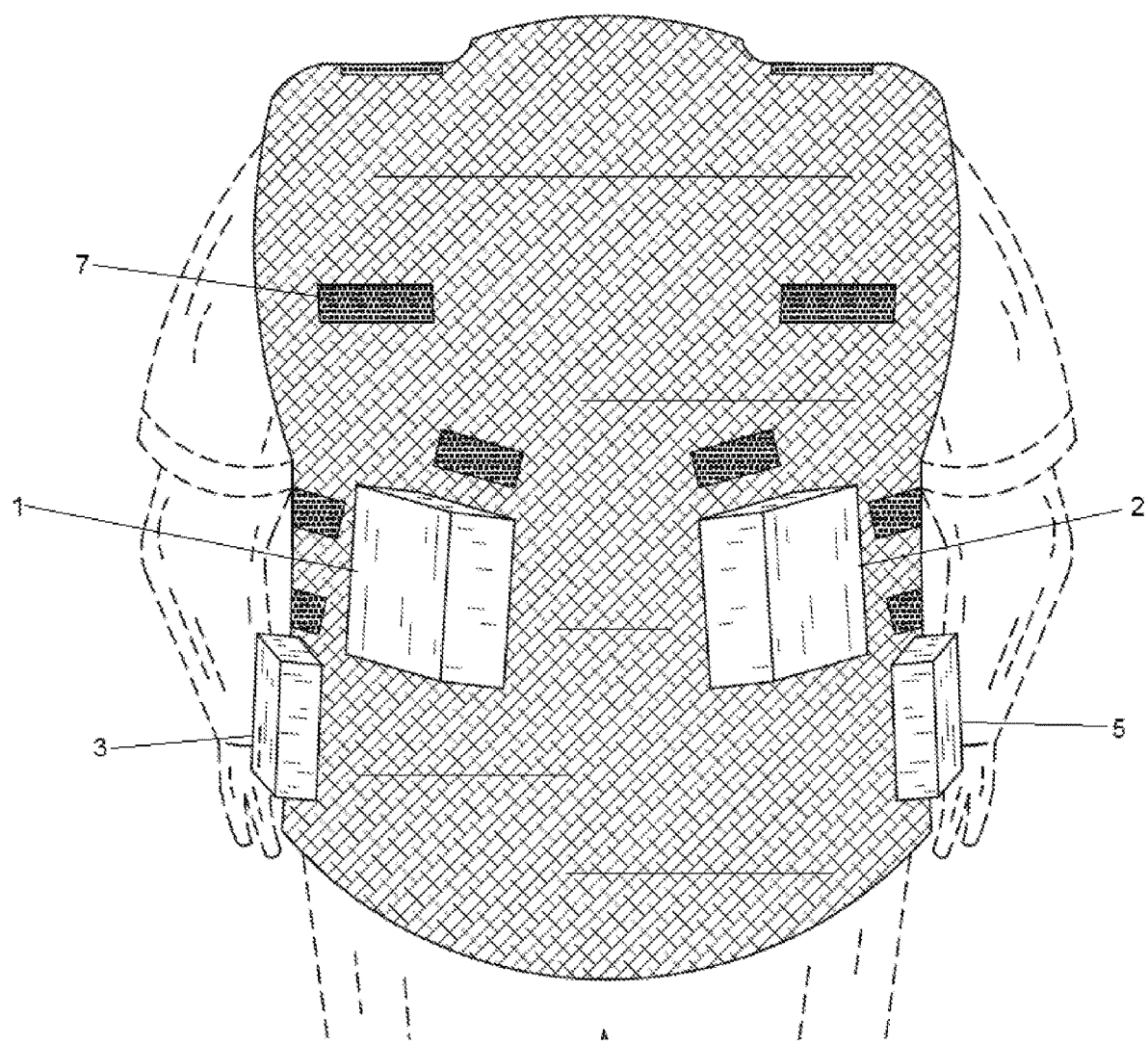
FIG. 14 depicts a back side view of the article shown in FIG. 10 being worn by a user.
Figure 15:
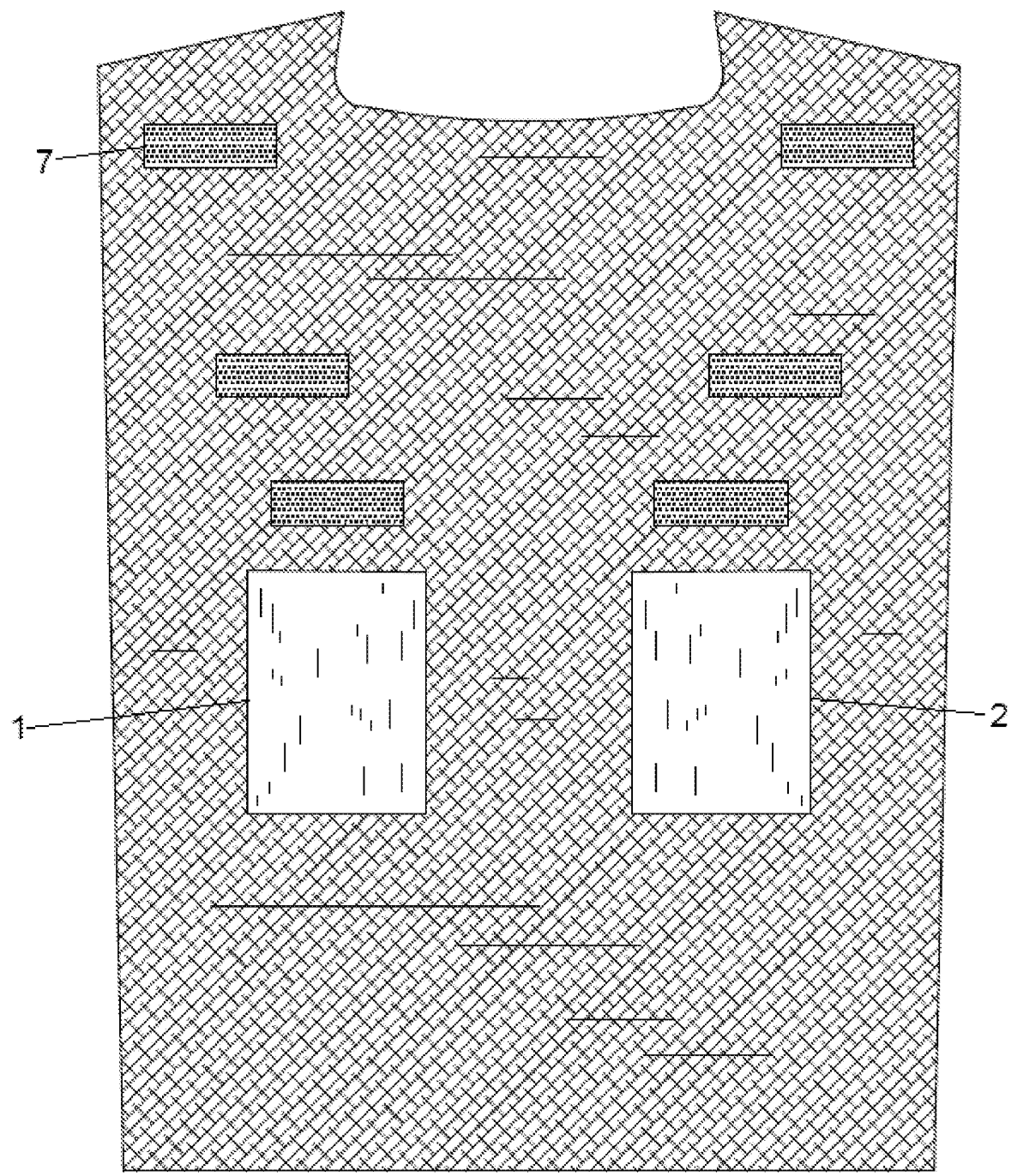
FIG. 15 depicts a back side view of the article shown in FIG. 10 in which the left and right sides of the vest are folded over the back of the vest.
Figure 16:
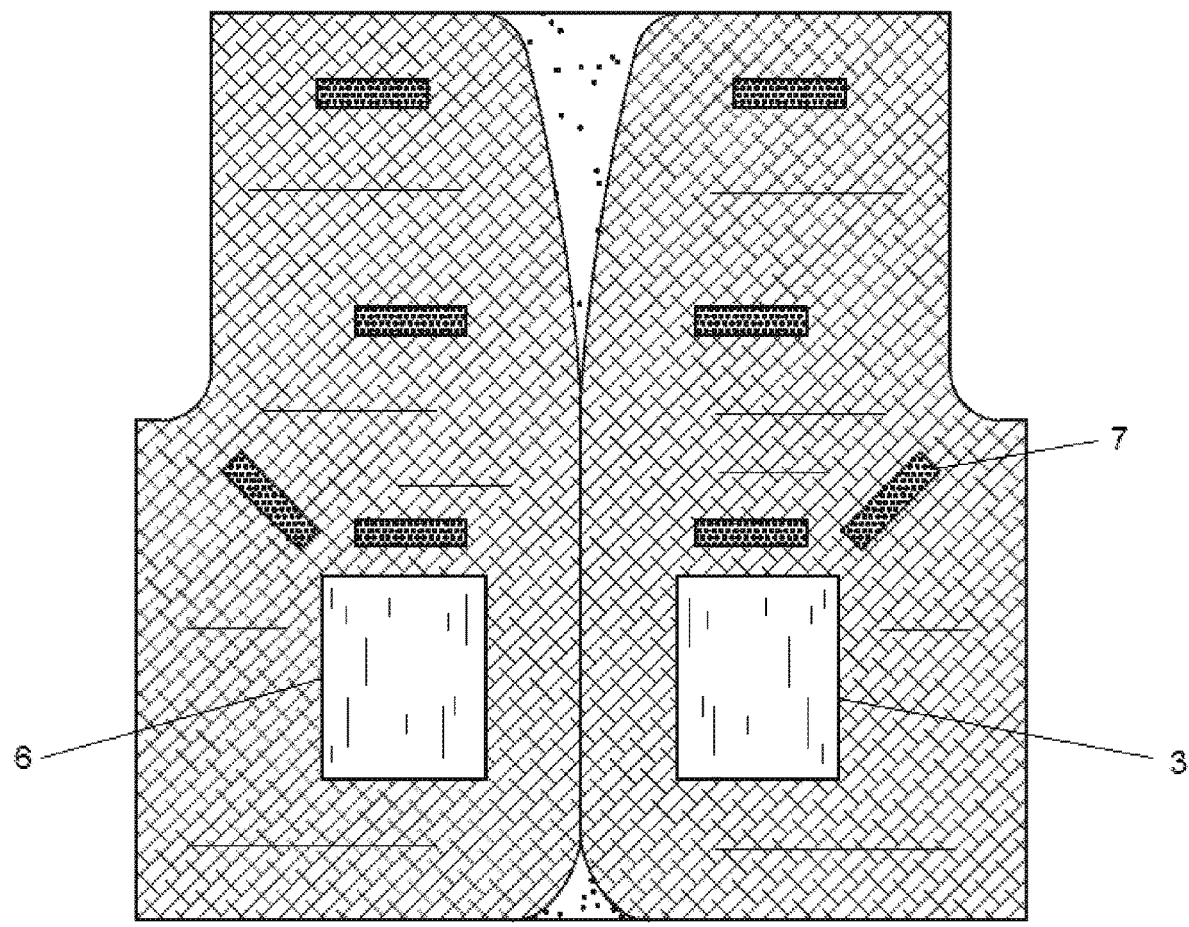
FIG. 16 depicts a front side view of the article shown in FIG. 10 in which the left and right sides of the vest are folded over the back of the vest.
Figure 17:
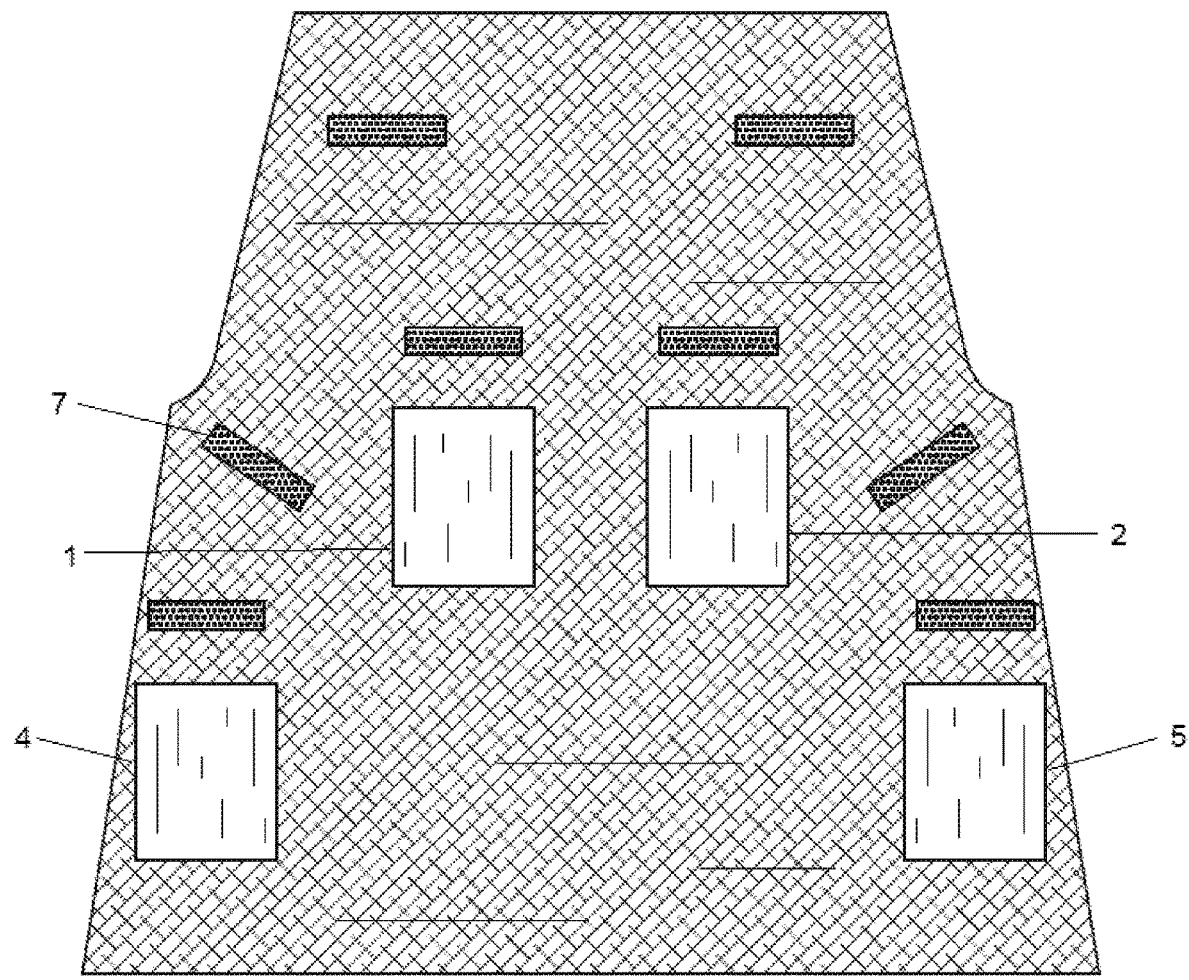
FIG. 17 depicts another back side view of the article shown in FIG. 10 in which the left and right sides of the vest are folded over the back of the vest.

FIG. 10 illustrates a six pocket vest in which the pockets are distributed about the vest such that when sensing devices are placed within the pockets of the vest, the sensing devices counter-balance each other. Two pockets (1, 2) are shown on the back (FIG. 10). Two pockets (3, 4) are shown on the left side (FIG. 14) and two pockets (5, 6) are shown on the right side (FIG. 14). When worn by a user, pockets 4 and 5 counter-balance each other (FIGS. 10-17) and pockets 3 and 6 wrap-around to the front of the vest to counter-balance pockets 1 and 2 (FIGS. 10-17). The embodiment shown in FIGS. 10-17 does not require weights for distributing the load of the vest evenly about a user. However, weights may optionally be introduced into any of the pockets, which may be helpful when sensing devices are of significantly different weights. Alternatively, not all of the pockets need to include sensing devices. In such embodiments, weights are put into the empty pockets to counter-balance the pockets that do include sensing devices.

In the embodiment shown in FIGS. 10-17, the vest includes straps that are capable of holding a conduit of the sensing device (e.g., tubing and/or wiring) against the vest and out of the way of the user (See reference number 7, which is the designator used for all straps shown in FIGS. 10-17, which are the rectangular dotted members shown in each of FIGS. 10-17. Only a single strap is labeled for clarity in FIGS. 10-17, but all of the rectangular dotted members in FIGS. 10-17 are straps.). On of skill in the art, will understand that straps are not a required component of this embodiment, and that the use of straps for retaining the conduit of the sensing device is only exemplary. Any retaining mechanism known in the art may be used to retain the conduit to the garment and to position a distal end of the conduit at a selected location on the wearer, for example within a personal breathing zone of a wearer. For example, in another embodiment, the vest includes integrated airtight channels and/or cables that are configured to provide a plug-in capability between the equipment that can be attached and an attachment unit, e.g., a sensor, an input/output (I/O) device, etc.

In the exemplary embodiment shown in FIGS. 10-17, the placement of the straps 7 for each of pockets 1-6 is arranged so that a conduit from can run from a sensing device to a separate location along the vest, for example the personal breathing zone of a user. The exemplary embodiments in FIGS. 10-17, the straps 7 associated with each of the pockets 1-6 are arranged so that conduit from each sensing device is positioned within personal breathing zone of a user. Such a configuration is only exemplary, and other placements of the straps may be used with articles of the invention.

The vest shown above in FIGS. 10-17 can be made by attaching 2" straps (7) and padded closeable pockets (1-6) with an approximate volume of 30 cubic inches to a class 2 safety vest. The following includes steps according to one embodiment for assembly and making of the vest. First attach the pockets (1-6) such that, when sensing devices are placed in the pockets, the load of the vest is evenly distributed about a user. Two pockets (1-2) are placed on the back of the vest. Two pockets (3-4) are placed on the left and two pockets (5-6) are placed on the right side of the vest. Next, attach straps 7 above each of the pockets 1-6. The straps are spaced about 3-7 inches apart, and continue up to the left and right shoulders of the vest.

Additionally, as depicted in FIGS. 1-4 and 10-17, the vest is constructed from a fabric with a bright color. The bright color provides improved visibility over the vests of prior art. The vest material can include polyester, cotton, plastic, flame resistant material (self-extinguishing/flame/heat resistant), reflective material, and high color contrast to background material. Flame resistant material is preferred for certain professions, such as welding, foundry work, electrical work, etc. Exemplary flame resistant materials used in clothing include polybenzimidazole (PBI), TWARON (flame-resistant para-aramid material, commercially available from Teijin Aramid), NOMEX (flame-resistant meta-aramid material, commercially available from DuPont), ARSELON (flame-resistant poly-oxa-diazole polymer material, commercially available from Khimvolokno), coated nylon, carbon foam, M5 fiber (polyhydroquinone-diimidazopyridine), KEVLAR (flame-resistant para-aramid synthetic material, commercially available from DuPont), PYROVATEX (flame-retardant finish for textiles of cellulose fibers and fabric blends based on a dialkylphosphono-carboxylic acid amide, commercially available from Ciba) impregnated material, TECHNORA (flame-resistant aramid material, commercially available from Teijin Aramid), and modacrylic fiber based materials (modified acrylic fibers made from acrylonitriles).

Various applications of the vest include sampling air for air quality monitoring, dosimetry in which an input device can measure noise and sound levels (decibel), radiation measuring in which a radiation sensor can be used to measure radiation, chemical and biological agent measurements in which a sensitized/functionalized sensor can measure presence of chemical/biological agents. In each of these cases, the presence of material/signal being measured can be measured and integrated over a period of time or a signal can be generated in which a threshold is met.

As discussed above, in each of the above-identified applications, interface between the sensor-I/O device and the equipment attached to the vest can be integrated into the vest. For example, the vest may be configured to include integrated air-tight channels that can be used to connect to a sensor at a point of connection to the sensor and connect to the attached equipment at a point of connection to the equipment. Alternatively, the vest may be configured to include integrated cable assemblies that can be used to connect to a sensor-I/O device at a point of connection to the sensor-I/O device and connect to the attached equipment at a point of connection to the equipment.

In certain embodiments, articles of the invention include a one or more lights positioned about the article. The lights may be used to help perform work tasks in dim lighting conditions or may be used to signal the location of the user to other workers.

In certain embodiment, the article is designed to easily pull apart, i.e., break away. Such a design is beneficial in the event that the article snags on something dangerous or hazardous while being worn by a user. For example, at industrial sites, there is typically a significant amount of machinery that users interact with, and an article of the invention could become caught in the machinery. Articles of the invention can be designed so that any portion of the article is designed to pull apart, and articles of the invention can be designed to pull apart at more than one location. Typically, pants can pull apart at two seams on the inside or outside of the legs. Shirts, jackets and anything else with sleeves can pull apart at two seams like pants, or one seam down the middle. Typically, one or two key seams are chosen to be made with affixing members (e.g., snaps or VELCO (hook and loop fasteners, commercially available from Velcro company)) instead of stitching. The members can be affixed (e.g., by stitching or hot gluing) at the open edges (breakaway-away areas) of the fabric. Generally, the affixing members, are positioned back from the very edge so that the garment will still hang naturally. The affixing members can be placed continuously along the seams or can be spaced apart (e.g., about 2 inches about or more). In embodiments in which the article is a vest, the break-away seams can be one or more shoulder portions, and/or the left and/or right side portions, and/or a seam positioned down the front and/or back of the vest, preferable down the middle of the front and/or back of the vest.

In other embodiments, just the portion of the a wearable garment that is configured to receive and releasably retain the sensing device is designed to break-away from the garment. In other embodiments, the portion of the a wearable garment that is configured to receive and releasably retain the sensing device is designed to break-away from the garment in addition to the wearable garment having one or more pull-apart seams.

In certain embodiments, the wearable garment is designed to adjustably fit to a user. For example, the garment can include cinches, straps, etc. so that a user is able to custom fit the garment to their body profile. In that manner, the article is prevented from loosely hanging from the user, which is important so that the article does not become caught in dangers or hazards around an industrial site, such as machinery. There can be more than one adjustable aspect to articles of the invention. For example, one or more adjustable mechanisms, such as cinches, can be set vertically into the article to adjust the length of the article. Alternatively or additionally, an one or more adjustable mechanisms, such as cinches, can be set horizontally (preferably around waist height) into the article to allow for tightening or loosening of the article around a wearer. As mentioned, the horizontal adjustment mechanism is preferably located to be in proximity to a user's hips, e.g., along a bottom portion of a vest or along a top portion of pants. In certain embodiments in which the article is pants, it may also be beneficial to have more than one horizontal adjustment mechanism, such as at the waist and at the bottom of each pant leg.

The adjustment mechanisms can be along inner portions of the article or can be along outer portions of the articles, for example, being affixed to the articles by hoops. In preferred embodiments, the adjustment mechanisms are within the article, and each article is configured so that excess straps or cinches can be inserted into the article after adjustment so that excess straps or cinches do not dangle outside the article. Alternatively, hoops outside the article can be used to contain excess straps against the article. In certain embodiments, the straps include VELCO (hook and loop fasteners, commercially available from Velcro company), so that excess straps may be attached to the adjustment mechanism after adjustment.

In certain embodiments, articles of the invention include a video camera. The video camera may be the sensing device, as already discussed above, or can be in addition to the sensing device. The video camera records and optionally transmits (optionally in real-time) images received to the camera. In certain embodiments, the camera is positioned to capture images of what the user is doing from their personal point of view. Such capability allows professionals to match exposure with individual tasks or locations. Any technique known in the art can be used to affix the video camera to the article, such as fasteners, glues, stitching, etc. The video camera can be set to continuous record images. Alternatively, the video camera can be set in a motion activation mode, such that it only begins recording images based on a motion signal received to the camera via a motion sensor operably associated with the camera. Motion sensitive recording conserves battery life as opposed to continuous recording. The camera can include a storage device, such as a micro SD card, that receives and stores recorded images for future viewing. Alternatively, the camera can include wireless hardware that allows the camera to transmit received images, optionally in real-time, to another location for optional real-time viewing. Exemplary cameras and mounts are sold by GoPro, Inc.

In certain embodiments, articles of the invention include a real-time tracking system, such as a radio frequency identification (RFID) tag, an indoor positioning system, or an outdoor global positioning system, etc. Equipping articles of the invention with a real-time tracking system allows a position of the article to be tracked in real-time. In certain embodiments, the real-time tracking system uses a radio frequency identification (RFID) tag. RFID is the wireless non-contact use of radio-frequency electromagnetic fields to transfer data, for the purposes of automatically identifying and tracking tags attached to objects. The tags contain electronically stored information. Some tags are powered by and read at short ranges (a few meters) via magnetic fields (electromagnetic induction). Others use a local power source such as a battery, or else have no battery but collect energy from the interrogating EM field, and then act as a passive transponder to emit microwaves or UHF radio waves (i.e., electromagnetic radiation at high frequencies). Battery powered tags may operate at hundreds of meters. Unlike a bar code, the tag does not necessarily need to be within line of sight of the reader, and may be embedded in the tracked object.

A radio-frequency identification system uses tags, or labels attached to the objects to be identified. Two-way radio transmitter-receivers called interrogators or readers send a signal to the tag and read its response.

RFID tags can be either passive, active or battery-assisted passive. An active tag has an on-board battery and periodically transmits its ID signal. A battery-assisted passive (BAP) has a small battery on board and is activated when in the presence of an RFID reader. A passive tag is cheaper and smaller because it has no battery. Tags may either be read-only, having a factory-assigned serial number that is used as a key into a database, or may be read/write, where object-specific data can be written into the tag by the system user. Field programmable tags may be write-once, read-multiple; "blank" tags may be written with an electronic product code by the user.

Typically, RFID tags contain at least two parts: an integrated circuit for storing and processing information, modulating and demodulating a radio-frequency (RF) signal, collecting DC power from the incident reader signal, and other specialized functions; and an antenna for receiving and transmitting the signal. The tag information is stored in a non-volatile memory. The RFID tag includes either a chip-wired logic or a programmed or programmable data processor for processing the transmission and sensor data, respectively.

An RFID reader transmits an encoded radio signal to interrogate the tag. The RFID tag receives the message and then responds with its identification and other information. This may be only a unique tag serial number, or may be product-related information such as a stock number, lot or batch number, production date, or other specific information.

RFID systems can be classified by the type of tag and reader. A Passive Reader Active Tag (PRAT) system has a passive reader which only receives radio signals from active tags (battery operated, transmit only). The reception range of a PRAT system reader can be adjusted from 1-2,000 feet, allowing flexibility in supervision. An Active Reader Passive Tag (ARPT) system has an active reader, which transmits interrogator signals and also receives authentication replies from passive tags. An Active Reader Active Tag (ARAT) system uses active tags awoken with an interrogator signal from the active reader. A variation of this system could also use a Battery-Assisted Passive (BAP) tag which acts like a passive tag but has a small battery to power the tag's return reporting signal. In certain embodiments, fixed readers are set up to create a specific interrogation zone that can be tightly controlled. That allows a highly defined reading area for when tags go in and out of the interrogation zone. Mobile readers may be hand-held or mounted on articles of the invention.

Signaling between the reader and the tag is done in several different ways, depending on the frequency band used by the tag. Tags operating on LF and HF bands are, in terms of radio wavelength, very close to the reader antenna because they are only a small percentage of a wavelength away. In this near field region, the tag is closely coupled electrically with the transmitter in the reader. The tag can modulate the field produced by the reader by changing the electrical loading the tag represents. By switching between lower and higher relative loads, the tag produces a change that the reader can detect. At UHF and higher frequencies, the tag is more than one radio wavelength away from the reader, requiring a different approach. The tag can backscatter a signal. Active tags may contain functionally separated transmitters and receivers, and the tag need not respond on a frequency related to the reader's interrogation signal.

An Electronic Product Code (EPC) is one common type of data stored in a tag. When written into the tag by an RFID printer, the tag contains a 96-bit string of data. The first eight bits are a header which identifies the version of the protocol. The next 28 bits identify the organization that manages the data for this tag; the organization number is assigned by the EPCGlobal consortium. The next 24 bits are an object class, identifying the kind of product; the last 36 bits are a unique serial number for a particular tag. These last two fields are set by the organization that issued the tag. Rather like a URL, the total electronic product code number can be used as a key into a global database to uniquely identify a particular product.

Often more than one tag will respond to a tag reader. Collision detection is important to allow reading of data. Two different types of protocols are used to "singulate" a particular tag, allowing its data to be read in the midst of many similar tags. In a slotted Aloha system, the reader broadcasts an initialization command and a parameter that the tags individually use to pseudo-randomly delay their responses. When using an "adaptive binary tree" protocol, the reader sends an initialization symbol and then transmits one bit of ID data at a time; only tags with matching bits respond, and eventually only one tag matches the complete ID string.

In certain embodiments, the real-time tracking system uses an indoor positioning system (IPS). IPS) or micromapping is a network of devices used to wirelessly locate objects or people inside a building. Instead of using satellites, an IPS relies on nearby anchors (nodes with a known position), which either actively locate tags or provide environmental context for devices to sense.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

EXAMPLES

Example 1: Field Test 1

Traditionally, industrial hygienist have had to place sampling trains on workers, which results in taking the worker away from his/her job for several minutes, and potentially uneasy feelings due the close personal contact needed to place the equipment on the individual. The objective of this study was to develop a sampling vest which ergonomically balances weight of the pump or dosimeter in one easy-on/easy-off self-contained vest/sampling train unit.

Three industrial hygienists and seven employees from three companies were asked to compare the donning of a lighter SKC AirLite (12 oz) sampling pump/sampling train to using the traditional method to using a sampling vest which contained a heavier SKC AirChek 52 (20 oz) pump. Additionally, twenty-six industrial hygiene students from Purdue University compared the vest to the traditional method in a simulated role playing scenario acting as both the industrial hygienist and the employee. All participants filled out a questionnaire about their experience.

The vest was significantly (p-value <0.0001) preferred by both industrial hygienists and employees compared to the traditional IH method even though the vest contained a heavier pump. The participants also indicated that the sampling vest was easier to use and took less time to distribute to employees than the traditional IH method. In addition participants indicated increased comfort in approaching/being approached to wear a sampling train.

The new sampling vest was more efficient, easier to use, and took less time to distribute. It eliminated the need for invading personal space to place the sampling train on the worker. In addition the use of the sampling vest made it easier to manage the sampling procedure if a worker needed to take a break.

Example 2: Field Test 2

Industrial Hygiene (IH) active sampling techniques with regard to placing a sampling train on the worker has not changed. Traditionally, an IH would explain to a worker why he/she was sampling and ask if it was alright to place the sampling equipment on him/her. The sampling pump would be placed on the belt of the worker with tubing leading to the sampling media which has been placed in the personal breathing zone located on the worker's shoulder area or lapel. There are a couple of problems which arise from this traditional IH method. Firstly, there is an inherent issue of awkwardness and potential sexual harassment which exists in placing the sampling train on the worker. In today's society people do not like being touched or touching other people. Secondly, the location and weight of the sampling equipment pulls on the worker's pants making for an uncomfortable experience which he or she will unlikely be willing to want to participate in again. Lastly, there is an inherent issue of looking incomplete or unprofessional with having to clip or duct tape the tubing on the worker's shirt. Duct taping looks unprofessional and the tape can peel off the shirt due to sweat, leading to tubing coming loose from the shirt and snagging on equipment which can lead to an accident.

The invention addresses those concerns by providing a sampling vest that is able to ergonomically hold the weight of the sampling train, making for a comfortable experience for the worker. The data show that a worker was more comfortable wearing a sampling vest that holds the sampling train, than the traditional sampling method of having the sampling train placed on him or her. The data further show that an industrial hygienist was more comfortable approaching a worker to wear the vest than the traditional IH method. The data further show that from the industrial hygienist perspective it was more comfortable to approach a worker and ask them to wear a sampling vest than to ask to place the sampling train on them directly. The data further show that using the sampling vest with the sampling equipment already on the vest took less time and be easier to distribute to the workers than the traditional IH method.

Twenty-seven industrial hygiene students at Purdue University who were learning how to approach a worker as an Industrial Hygienist and place particulate sampling trains on them using the traditional IH method voluntarily compared the traditional IH methods with that of using a sampling vest. The students were asked to experience being a "worker" and have another industrial hygiene student place a sampling train on them using the traditional IH method, and then experience being the Industrial hygienist and place the sampling train on another student.

Figure 7:
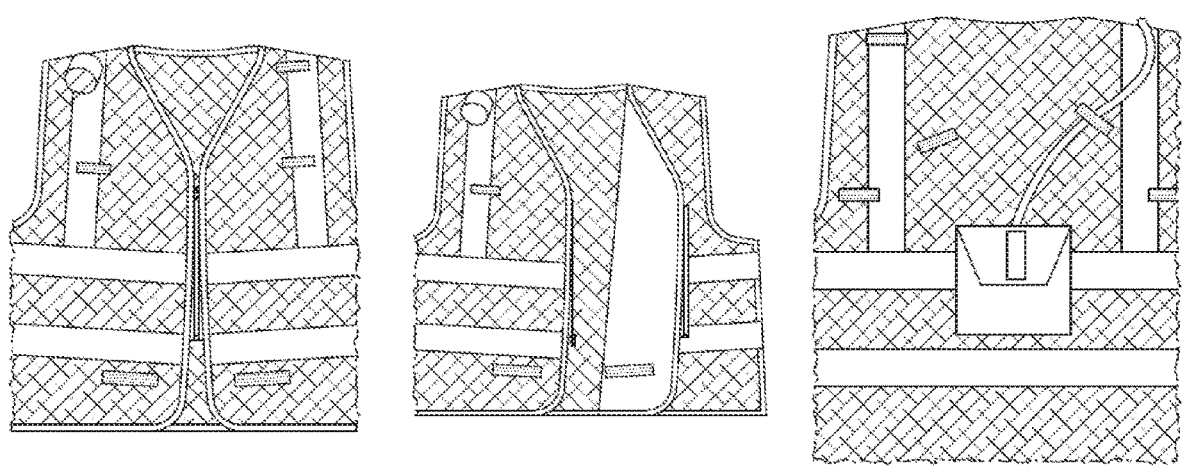
FIG. 7 shows different views of an embodiment of the invention.

The pumps which were used in the Traditional IH method were the SKC AirLite pumps. The students were then asked to perform the same tasks, but using the prototype sampling vest. The sampling vest had a padded back pocket which housed an SKC AirChek 52 pump. The sampling vest also had Velcro straps which held the tubing close to the vest eliminating the use for clips and duct tape. Additionally the vest technology had integrated front weights to counterbalance the weight of the pump, making for a more comfortable experience for the wearer. The vest is shown in FIG. 7.

After the students had tested both methods (traditional IH and sampling vest), they were asked to fill out a questionnaire about their experience as both an Industrial Hygienist and "Worker" with regards to comfort and ease of use. The results were analyzed using a paired t-test, results of which are shown in Table 1 below.

TABLE 1 t-Test: Paired Two Sample for Means

|  | IH Method | Sampling Vest |
|---|---|---|
| Mean | 3.43 | 4.68 |
| Valiance | 1.22 | 0.30 |
| Observations | 28 | 28 |
| t Stat | −6.35 | |
| P (T <= t) one-tail | <0.0001 | |
| t Critical one-tail | 1.70 | |
| P (T <= t) two-tail | <0.0001 | |
| t Critical two-tail | 2.05 | |

Figure 8:
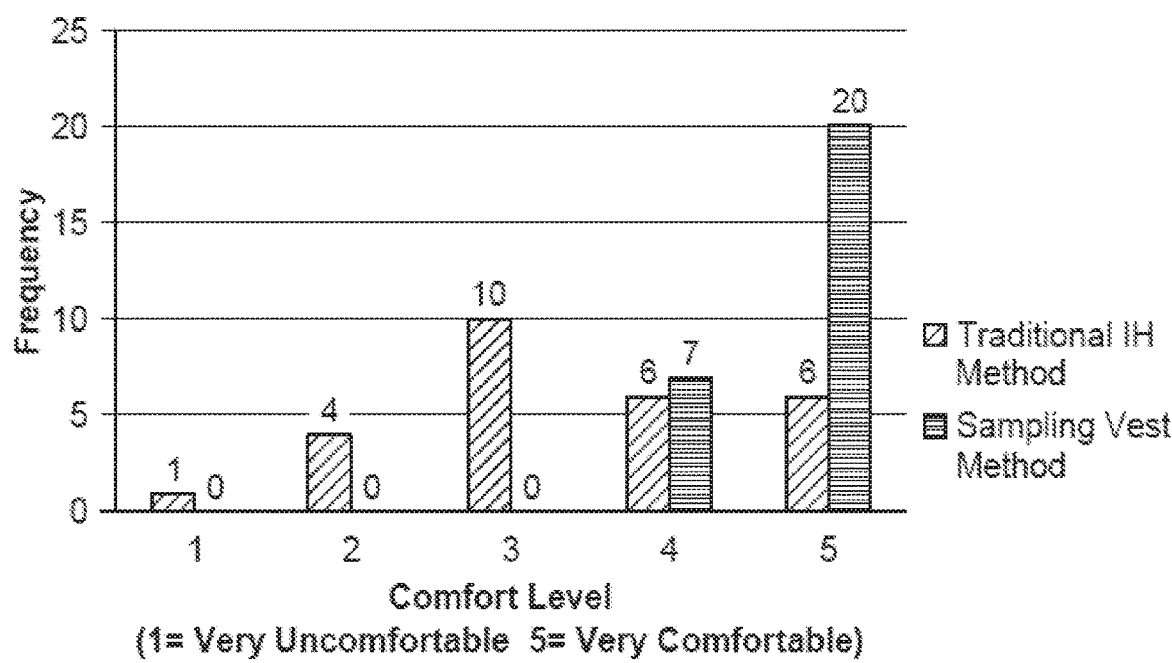
FIG. 8 is a graph illustrating comfort of placing a sampling train on a worker from the perspective of an industrial hygienist.
Figure 9:
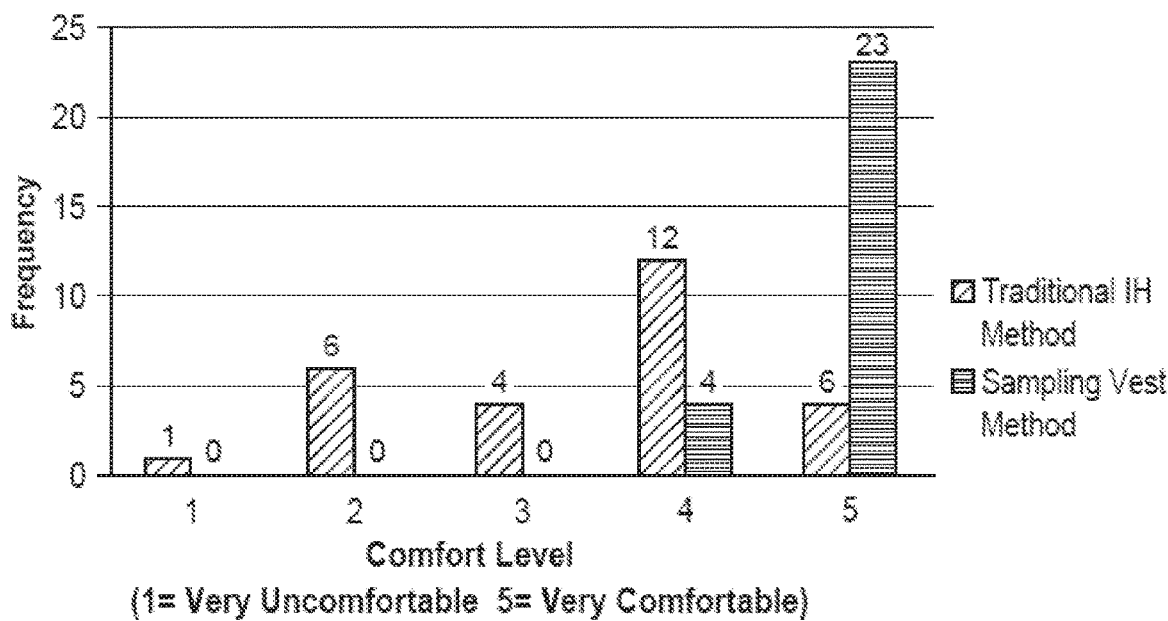
FIG. 9 is a graph illustrating comfort of having a sampling train placed on work from the worker's perspective.

Additional results are also shown in FIGS. 8-9. Those results show that using the new sampling vest was significantly (P-Value=<0.0001) more comfortable from the worker's perspective than the traditional IH method of place the sampling train directly on them. The results show that from the Industrial Hygienist perspective it was significantly (P-Value=<0.0001) more comfortable to have a worker wear the sampling vest than to place the sampling train on the worker. 100% respondents indicated that it was easier to the sampling vest than to place the sampling train on the worker. 100% of respondents indicated that it takes less time to distribute to a worker than traditional IH method. 100% of respondents would use the vest in the future and recommend them to other Industrial Hygiene professionals. Additionally 100% of respondents said that compared to the traditional IH method the sampling vest was easier to use, took less time to distribute to workers, would prefer to use them in the future, and would recommend them to other IH professionals.

What is claimed is:

1. An article of clothing, the article comprising: a wearable garment and at least one sensing device, wherein the sensing device comprises a body coupled to a conduit, and the garment is configured to releasably hold the body of the sensing device, to retain the conduit to the garment, and to position a distal end of the conduit within a personal breathing zone of a wearer.

2. The article according to claim 1, wherein the article is a vest.

3. The article according to claim 2, wherein the vest comprises a pocket and the body of the sensing device is held within the pocket.

4. The article according to claim 3, wherein the pocket comprises a flap.

5. The article according to claim 4, wherein the pocket is on a back of the vest.

6. The article according to claim 5, wherein the vest comprises an open channel between inner and outer layers of the vest, and the conduit passes through the channel from the pocket to a distal opening of the channel at a top portion of the vest such that a distal end of the conduit is within the personal breathing zone of the wearer.

7. The article according to claim 5, wherein the vest comprises a plurality of tabs attached to an outer layer of the vest, and the conduit passes through the tabs from the pocket such that a distal end of the conduit is within the personal breathing zone of the wearer.

8. The article according to claim 3, wherein the conduit is selected from the group consisting of a tube and an electrical wire.

9. The article according to claim 1, wherein the sensing device is selected from the group consisting of: a sampling pump, a noise dosimeter, a radiation sensor, a chemical sensor, a biological agent sensor, a video camera, and a combination thereof.

* * * * *